(12) United States Patent
McFadden

(10) Patent No.: US 6,179,846 B1
(45) Date of Patent: Jan. 30, 2001

(54) SURGICAL HEAD CLAMPING DEVICE

(75) Inventor: Joseph T. McFadden, 450 E. Lionhead Cir., Vail, CO (US) 81657

(73) Assignee: Joseph T. McFadden, Vail, CO (US)

( * ) Notice: Under 35 U.S.C. 154(b), the term of this patent shall be extended for 0 days.

(21) Appl. No.: 09/397,860

(22) Filed: Sep. 17, 1999

(51) Int. Cl.[7] .................................................. A61B 19/00
(52) U.S. Cl. ............................................ 606/130; 602/37
(58) Field of Search .......................... 606/130; 128/869; 602/36, 37, 32, 40, 39, 17

(56) References Cited

U.S. PATENT DOCUMENTS

| | | | |
|---|---|---|---|
| 1,967,471 | * 7/1934 | Ettinger | .................................... 602/37 |
| 2,266,628 | * 12/1941 | Finochietto | ............................. 602/36 |
| 2,494,792 | * 1/1950 | Bloom | ...................................... 602/37 |
| 2,966,383 | * 12/1960 | Boetcker et al. | . |
| 3,654,923 | * 4/1972 | Crutchfield | .............................. 602/37 |
| 4,108,426 | * 8/1978 | Lindstroem et al. | . |
| 4,501,267 | * 2/1985 | Pecheux | . |
| 5,330,485 | * 7/1994 | Clayman et al. | ...................... 606/130 |

FOREIGN PATENT DOCUMENTS

1171021 * 8/1985 (SU) ...................................... 602/37

* cited by examiner

Primary Examiner—Jeffrey A. Smith
(74) Attorney, Agent, or Firm—W. Warren Taltavull; Farkas & Manelli PLLC

(57) ABSTRACT

A patient head clamp is provided with two pairs of interconnected arms arranged so that the sleeves carrying skull penetrating pins will maintain the pins in alignment with the limits of the spatial separation of the arms of clamp.

8 Claims, 3 Drawing Sheets

SURGICAL HEAD CLAMPING DEVICE

FIELD OF THE INVENTION

This invention relates to head or skull clamping and holding devices used in surgery on the head of a patient and, more specifically, to an improved design for such devices that facilitates placement of the head in the clamp so as to more securely hold the head in position during a surgical procedure and allow adjustment of the head during an operation.

BACKGROUND OF THE INVENTION

It has long been the practice in neurosurgery to employ a three point clamp on the head of a patient to securely locate and hold the head in place during surgery. In the prior art devices, pins mounted on one or more adjustable arms are forced into the skull of the patient to positively grip the skull so that subsequent movement is not possible. This is important in neurosurgery since, in many procedures, the patient is not fully sedated but remains conscious to enable responses to probes to be evaluated by the medical staff.

The use of three arms to support three penetrating pins introduces a complication that has proved unnecessary in the installation of the prior art skull clamps. This is the case primarily because such clamps could not provide accurate alignment of two of the skull engaging pins for all head sizes. In many arrangements, there was no possibility of aligning two oppositely disposed pins. In other systems, the ability to align two of the pins relied on the use of complicated structure that occupied an unacceptable amount of space in the vicinity of the patient's skull and was difficult to both put in place and to adjust during a surgical procedure. It is well recognized that surgical staff must have the maximum space available to move about a patient during surgery particularly in the event of unforeseen complications arising. With several available clamping apparatus, freedom of movement about the patient was curtailed due to the obstructions caused by the skull clamping apparatus.

SUMMARY OF THE INVENTION

The present invention provides a surgical head clamp that is much easier to install in a secure manner. Also, while providing three point contact, the clamp of the present invention utilizes a much simpler support structure which will maximize the maneuvering space in the vicinity of the patient's head available to the surgeon and support staff.

The foregoing objects are attained by providing two pairs of articulatable arms with each pair having one end pivotally mounted on a single yoke. The opposite or free ends of each pair on one side of the yoke carries a pivot mount for a pin carrier which is typically a threaded bore and which receives a skull engaging pin. Each articulatable arm is provided with a plurality of threaded bores for accommodating a third pin. Structure is provided to ensure that the pins carried by the pivot mount on the arms are maintained in substantially perfect alignment whatever the separation of the free ends of the arms. This is accomplished without compromising the simplicity of the clamping structure so that a maximum maneuvering space will be afforded the surgeon and medical staff during a surgical procedure. Also, installation of clamp will be much simpler than the three arm clamps of the prior art while allowing the clamp to accommodate the same or a much greater range of skull sizes.

These advantages as well as others will become apparent as consideration is given to the following description and accompanying drawings, in which:

DETAILED DESCRIPTION OF THE INVENTION

Figure 1:
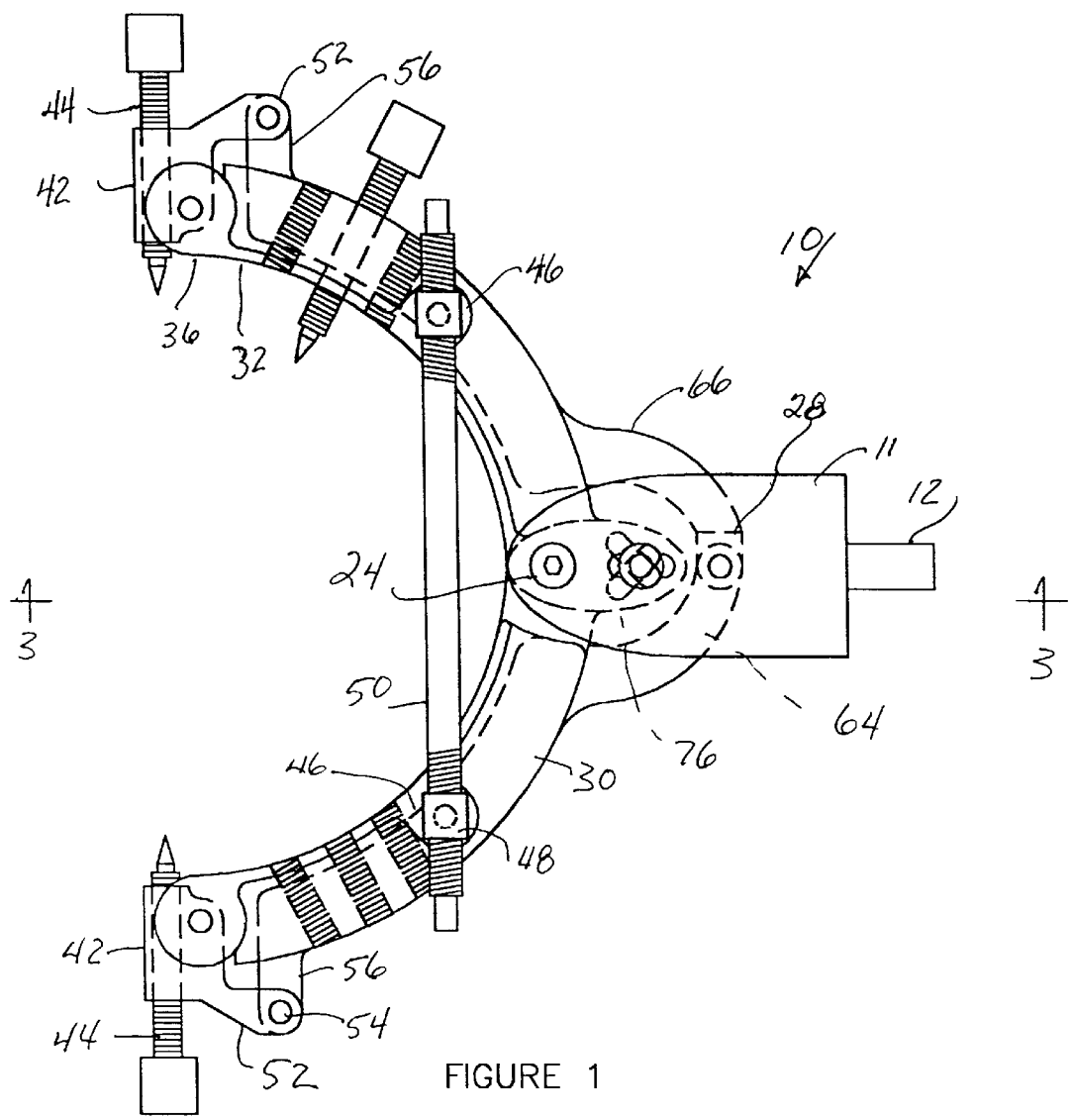
FIG. 1 is an elevational view of one side of the clamp.
Figure 3:
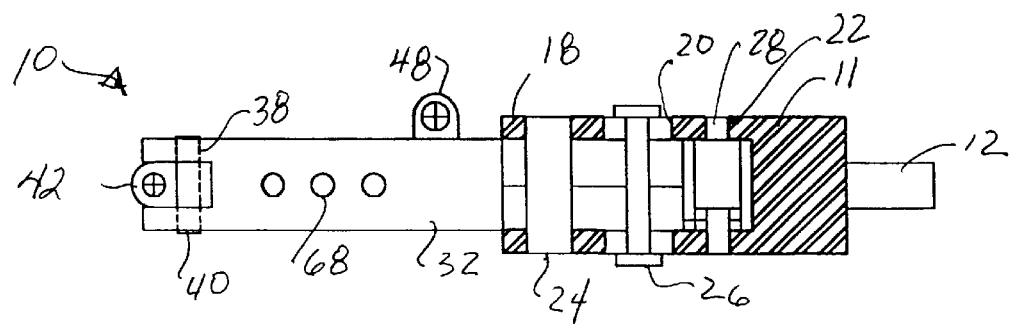
FIG. 3 is a sectional view taken along lines 3—3 of FIG. 1.

Referring to the drawings, there is shown in FIGS. 1 and 3, an elevational view of one face of the clamp 10 of the present invention and a sectional view along lines 3—3 FIG. 1. The clamp 10 includes a yoke or base member 11 which, as is shown more clearly in FIG. 3, is provided with two spaced apart arms 14 and 16 which extend substantially parallel to one another. The bottom surface of the base 11 is provided with a rigid post 12 which is typically provided to permit insertion into a support arm extending from the operating table which may be of the type disclosed in U.S. Pat. Nos. 4,964,748 or 5,560,728.

The faces 14 and 16 of the base 11 are provided with aligned apertures as at 18, 20 and 22 for receiving pivot pins such as shown at 24, 26 and 28. Mounted on pivot pins 24 and 26 are the inner ends of a first pair of articulated arms 30 and 32. The opposite ends of the arms 30 and 32 may be bifurcated as shown in FIG. 3 to provide a secure mount for a pin support body 42. Also, the ends are formed as enlarged portions 34 and 36 which are apertured as at 38 to receive a pivot pin 40 which supports the pin support body 42. The support body 42 adjustably carries a skull engaging or anchor pin 44 in the threaded bore 47 of the body 42.

Intermediate their respective ends, each of the arms 30 and 32 is provided with an integral platform 46 which carries a threaded sleeve 48 for cooperation with the threaded portions of a spacer bar 50. Rotation of the bar 50 will effect and regulate the pivoting movement of the arms 30 and 32 about the axis 24 of the base 11. A separate tool will be provided to effect rotation of the bar 50. Preferably, the sleeves 48 are rotatable on the platforms to maintain alignment with the bar 50 during movement of the arms 30 and 32. In an alternate arrangement, the bar 50 can be replaced by internally threaded sleeve which has one end pivotally mounted on one sleeve 48 of arm 30 and a threaded rod which has one end mounted in the sleeve 48 on the other arm 32. The rod will be threaded into and out of the internally threaded sleeve to move the arms 30 and 32 towards and away from each other. A spring detent may be installed in the internally threaded sleeve to provide resistance to threading as a safety measure.

Each pin supporting body 42 is formed with a depending extension 52 which are each pivotally connected by a respective pin 54 to the bifurcated end 56, 58 of a respective, second articulated arm 60,62. The depending extension of each body 42 is selected so as to position and, as explained below, maintain the axis of each sleeve 42 aligned. With this arrangement, the points of each skull engaging pin 44 will always be in axial alignment, that is, opposite one another, for all spacings of the arms 30, 32 and 60,62. To accomplish this, in addition to the spatial displacement between the axis of pins 40 and 54, the pivot pin 28 on which the opposite ends 64 and 66 of arms 60,62 are attached is spaced a distance from the pivot pin 24 of arms 30, 32. The magnitude of these distances must be selected with the view to maintaining the axis of each sleeve 42 in alignment with axis 70 which passes through each point of pins 44. With such a disposition, the points of pins 44 will be substantially or exactly opposite each other when inserted into the skull of a patient for all positions of the respective arms.

Figure 2:
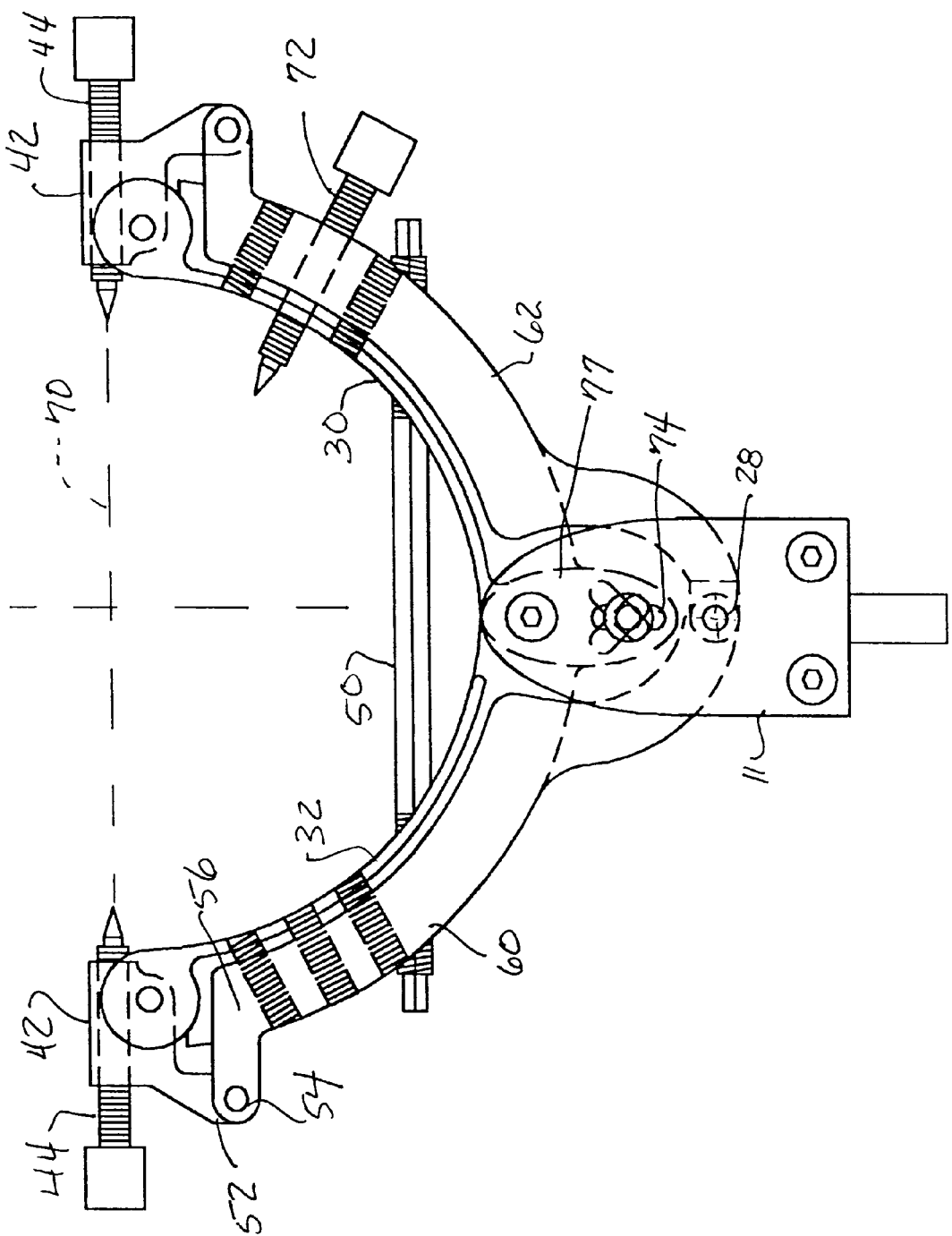
FIG. 2 is a view similar to FIG. 1 but showing the opposite side of the clamp.
Figure 4:
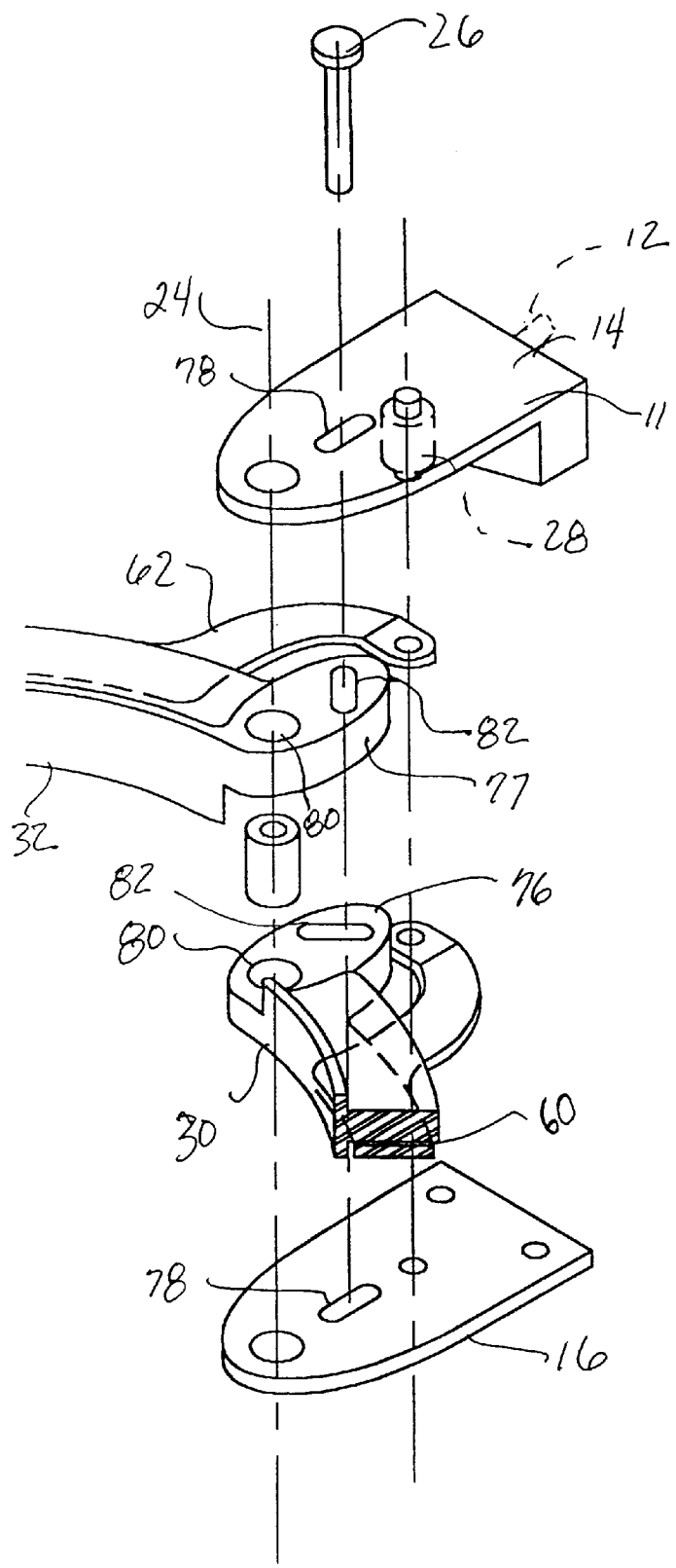
FIG. 4 is an exploded view of the yoke and attachment ends of the arms.

Preferably, to reduce the protrusion of members into or adjacent the operation site, the arms 60 and 62 are configured to closely underlie the arms 30, 32 as shown more clearly in FIGS. 2 and 4. This disposition will require that the inner ends 64, 66 of the arms 60 and 62 depart from the smooth arcuate curvature of the major portion of each arm at a point adjacent to the faces 14, 16 of the base 11 and to assume a second curvature to the ends that are mounted on the pivot pin 28.

A limit pin 26 is provided between pins 22 and 24 and which extends through an elongated slot 78 formed in each of the faces 14 and 16 in the base 11. Each arm 30, 32 at its inner end is formed with pivot bore 80 through which extends the pivot pin 24. An extension arm 76, 77 is provided on the inner end of each arm 30,32 and each arm 76,77 is formed with an angled slots 82 through which limit pin 26 extends and is moved in its slots 74. The axial extent of the slot 74 limits the spreading of the pairs of arms 30,32 in which the pin 26 is free to move. Limiting movement of the arms 30,32 and by virtue of their interconnection, of the arms 60,62, is effected by the positioning of the slots 74 in the extension arms 76, 77 provided at the inner ends of arms 30,32.

For assured stability of the patient's head, a plurality of threaded bores, one of which is indicated at 68, are formed in arms 30, 32 for the purpose of receiving a third skull pin 72. The surgeon will select the appropriate bore 68 to use and this will depend on the size of the patient's skull.

Having described the invention, it will be apparent that various modifications can be made therein without departing from the spirit and scope of the invention.

What is claimed is:

1. A head clamping device for surgery or the like comprising a pivot base, a first and a second arm each having one end pivotably mounted on a first pivot pin on said pivot base and each extending arcuately away from said pivot base, each of said first and second arms terminating in a yoke with a support member pivotally mounted in each said yoke on a pivot pin, each support member including a leg member, said device including a third and a fourth arm each having one end pivotally mounted adjacent said pivot base and an opposite end pivotally attached to a leg member of one of said support members.

2. The device as claimed in claim 1 wherein said third and fourth arms are each shaped to extend arcuately from adjacent said pivot base to said respective support member.

3. The device as claimed in claim 2 wherein said third and fourth arms each include an extension having a end with said ends of said extensions being pivotally joined at a position spaced from said pivot base.

4. The device as claimed in claim 1 wherein each said support member supports a penetration pin.

5. The device as claimed in claim 1 wherein said first and second arms intermediate their respective ends include an adjustment member connecting said first and second arms together.

6. The device as claimed in claim 5 wherein said adjustment member includes threaded portions and said arms each include a threaded bore receiving a said threaded portion of said adjustment member whereby rotation of said adjustment member relative to a said bore effects movement of said first and second arms toward or away from each other.

7. The device as claimed in claim 1 wherein said first and second arms each have a plurality of apertures of substantially the same size and said third and fourth arms each have a plurality of apertures of substantially the same size with the apertures of the first and third arms and the second and fourth arms being respectively alignable for a set of pivot positions of said first and second arms.

8. The device as claimed in claim 1 wherein said one end of each of said first and second arms are each formed with an enlarged extension formed with a through slot with the slot in one enlarged extension extending at an angle to the slot formed in the other enlarged extension with a pin extending through said slots to limit the angular position assumable by said first and second arms relative to said pivot base.

* * * * *